United States Patent [19]

Woosley et al.

[11] Patent Number: 5,375,693

[45] Date of Patent: Dec. 27, 1994

[54] METHODS AND COMPOSITIONS FOR TREATING ALLERGIC DISORDERS AND OTHER DISORDERS METABOLIC DERIVATIVES OF TERFENADINE

[75] Inventors: Raymond L. Woosley, Washington, D.C.; James W. Young, Still River, Mass.; Yiwang Chen, Silver Spring, Md.

[73] Assignees: Sepracor, Inc., Marlboro, Mass.; Georgetown University, Washington, D.C.

[21] Appl. No.: 191,061

[22] Filed: Feb. 2, 1994

Related U.S. Application Data

[63] Continuation of Ser. No. 924,156, Aug. 3, 1992, abandoned.

[51] Int. Cl.$^5$ .............................. A61K 31/445
[52] U.S. Cl. .................................... 514/317
[58] Field of Search ........................... 514/317

[56] References Cited

U.S. PATENT DOCUMENTS 4,254,129 3/1981 Carr et al. .................... 424/267

FOREIGN PATENT DOCUMENTS

WO94/03170 of 1994 WIPO .

OTHER PUBLICATIONS

Zamani et al., *Chemical Abstracts*, CA116(17):165681z, 1991.

*Primary Examiner*—Raymond Henley, III
*Assistant Examiner*—William Jarvis
*Attorney, Agent, or Firm*—Pennie & Edmonds

[57] ABSTRACT

Methods and compositions are disclosed utilizing metabolic derivatives of terfenadine for the treatment of allergic disorders while avoiding the concomitant liability of adverse effects associated with the terfenadine. The metabolic derivatives of terfenadine are also useful for the treatment of retinopathy and other small vessel disorders associated with diabetes mellitus and such other conditions as may be related to the antihistamine activity of terfenadine. For example, the metabolic derivatives of terfenadine are useful for the treatment of asthma, motion sickness, and vertigo, without the concomitant liability of adverse effects associated with terfenadine. Furthermore, the metabolic derivatives of terfenadine, in combination with non-steroidal anti-inflammatory agents or other nonnarcotic analgesics, or in combination with a decongestant, cough suppressant-/antitussive or expectorant, are useful for the treatment of cough, cold, cold-like, and/or flu symptoms and the discomfort, headache, pain, fever, and general malaise associated therewith, without the concomitant liability of adverse effects associated with terfenadine.

6 Claims, No Drawings

METHODS AND COMPOSITIONS FOR TREATING ALLERGIC DISORDERS AND OTHER DISORDERS METABOLIC DERIVATIVES OF TERFENADINE

This is a continuation of Ser. No. 07/924,156 filed on Aug. 3, 1992 now abandoned.

BACKGROUND OF THE INVENTION

This invention relates to novel pharmaceutical compositions containing 4-[1-hydroxy-4-(4-hydroxydiphenylmethyl-1-piperidinyl)butyl]-α,α-dimethylbenzeneacetates and 1-[p-(2-hydroxymethyl-2-propyl)phenyl]-4-[4-(α-hydroxy-α-phenylbenzyl)-1-piperidinyl]butanol. These compositions possess potent antihistaminic activity and are useful in treating allergic rhinitis, asthma and other allergic disorders while avoiding adverse effects associated with the administration of other α-aryl-4-substituted piperidinoalkanol derivatives, such as terfenadine, including but not limited to cardiac arrhythmias, drowsiness, nausea, fatigue, weakness and headache. Also, these compositions, in combination with non-steroidal anti-inflammatory agents or other non-narcotic analgesics, are useful for the treatment of cough, cold, cold-like, and/or flu symptoms and the discomfort, headache, pain, fever, and general malaise associated therewith. The aforementioned combinations may optionally include one or more other active components including a decongestant, cough suppressant/antitussive, or expectorant.

Additionally, these novel pharmaceutical compositions containing 4-[1-hydroxy-4-(4-hydroxydiphenylmethyl-1-piperidinyl)butyl]-α,α-dimethylbenzeneacetates and 1-[p-(2-hydroxymethyl-2-propyl)phenyl]-4-[4-(α-hydroxy-α-phenylbenzyl)-1-piperidinyl]butanol are useful in treating motion sickness, vertigo, diabetic retinopathy, small vessel complications due to diabetes and such other. conditions as may be related to the activity of these derivatives as antagonists of the H-1 histamine receptor while avoiding the adverse effects associated with the administration of other α-aryl-4-substituted piperidinoalkanol derivatives, such as terfenadine.

Also disclosed are methods for treating the above-described conditions in a human while avoiding the adverse effects that are associated with the administration of other α-aryl-4-substituted piperidinoalkanol derivatives, such as terfenadine, by administering the aforementioned pharmaceutical compositions containing 4-[1-hydroxy-4-(4-hydroxydiphenylmethyl-1-piperidinyl)butyl]-α,α-dimethylbenzeneacetates and 1-[p-(2-hydroxymethyl-2-propyl)phenyl]-4-[4-(α-hydroxy-α-phenylbenzyl)-1-piperidinyl]butanol to said human.

The active compounds of these compositions and methods are metabolic derivatives of terfenadine. Chemically, these derivatives are methyl 4-[1-hydroxy-4-(4-hydroxydiphenylmethyl-1-piperidinyl)butyl]-α,α-dimethylbenzeneacetate, 4-[1-hydroxy-4-(4-hydroxydiphenylmethyl-1-piperidinyl)butyl]-α,α-dimethylbenzeneacetic acid, and 1-[p-(2-hydroxymethyl-2-propyl)phenyl]-4-[4-(α-hydroxy-α-phenylbenzyl)-1-piperidinyl]butanol. These compounds are described in Garteiz et al., *Arzneimittel-Forschung/Drug Research*, 32: 1185–1190 (1982).

Terfenadine is an antagonist of the H-1 histamine receptor protein. Histamine receptor proteins occur in two well-identified forms in tissues as H-1 and H-2 receptors. The H-1 receptors are those that mediate the response antagonized by conventional antihistamines. H-1 receptors are present in the guinea pig ileum, the skin of Rhesus monkeys, and the bronchial smooth muscle of guinea pig. Terfenadine antagonizes the effect of histamine in the guinea pig isolated ileum, suppresses histamine-induced whealing in the skin of Rhesus monkeys, and protects against histamine induced lethality in the guinea pig.

Through H-2 receptor-mediated responses, histamine stimulates gastric acid secretion in the guinea pig and the chronotropic effect in isolated guinea pig atria. Terfenadine has no effect on histamine-induced gastric acid secretion, nor does it alter the chronotropic effect of histamine on atria. Thus, terfenadine has no apparent effect on the H-2 histamine receptor. See Cheng et al., *Drug Development Research*, 2:181–196 (1982).

Terfenadine is well absorbed but is extensively metabolized. See Okerholm et al., *Biopharmaceutics and Drug Distribution*, 2:185–190 (1981). Two main metabolites have been identified and one of the metabolites, 4-[1-hydroxy-4-[4-(hydroxydiphenylmethyl-1-piperidinyl)butyl]-α,α-dimethylbenzeneacetic acid, is reported to have antihistaminic activity. See Gartiez et al., *Arzneimittel-Forschung/Drug Research*, 32:1185–1190 (1982).

On the basis of its antihistaminic activity, researchers evaluated the effect of terfenadine in the treatment of allergic rhinitis. Clinical trials of efficacy indicated that terfenadine is slightly less effective than chlorpheniramine, another H-1 antagonist. See Connell, *Pharmacotherapy*, 5:201–208 (1985).

It has also been suggested that terfenadine would be useful for the treatment of asthma. In guinea pigs, the increase in airway resistance caused by $LTD_4$ (leukotriene $D_4$) was suppressed by terfenadine. See Akagi et al., *Oyo Yakuri*, 35:361–371 (1988).

Terfenadine may also be useful for the treatment of motion sickness and vertigo. Some antihistamines have been found to be effective for the prophylaxis and treatment of motion sickness. See Wood, *Drugs*, 17:471–479 (1979). Some antihistamines have also proven useful for treating vestibular disturbances, such as Meniere's disease, and in other types of vertigo. See Cohen et al., *Archives of Neurology*, 27:129–135 (1972).

In addition, terfenadine may be useful in the treatment of diabetic retinopathy and other small vessel disorders associated with diabetes mellitus. In tests on rats with streptozocin-induced diabetes, treatment by antihistamines prevented the activation of retinal histamine receptors which have been implicated in the development of diabetic retinopathy. The use of antihistamines to treat retinopathy and small vessel disorders associated with diabetes mellitus is disclosed in U.S. Pat. No. 5,019,591.

It has also been suggested that terfenadine, in combination with non-steroidal anti-inflammatory agents or other non-narcotic analgesics, would be useful for the treatment of cough, cold, cold-like and/or flu symptoms and the discomfort, pain, headache, fever, and general malaise associated therewith. The use of pharmaceutical compositions containing terfenadine and non-narcotic analgesics or non-steroidal anti-inflammatory agents such as aspirin, acetaminophen, and ibuprofen are described in U.S. Pat. Nos. 4,783,465 and 4,829,064. These compositions for the treatment of the above-described symptoms may optionally include one or more other active components including a decongestant (such as pseudoephedrine), a cough suppressant/antitussive (such as dextromethorphan) or an expectorant (such as guaifenesin).

Many antihistamines cause somewhat similar adverse effects. These adverse effects include but are not limited to sedation, gastrointestinal distress, dry mouth, and constipation or diarrhea. Terfenadine has been found to cause relatively less sedation, gastrointestinal distress, dry mouth, and constipation or diarrhea, as compared with other antihistamines.

However, the administration of terfenadine to a human has been found to cause other adverse effects. These adverse effects include but are not limited to cardiac arrhythmias, including ventricular tachyarrhythmias, torsades de pointes, and ventricular fibrillation. Recently, clinical practitioners have noted an increase in the occurrence of these cardiac arrhythmias upon coadministration of terfenadine with other drugs such as ketoconazole and erythromycin or upon overdose of terfenadine.

Thus, it would be particularly desirable to find a compound with the advantages of terfenadine which would not have the aforementioned disadvantages.

SUMMARY OF THE INVENTION

It has now been discovered that methyl 4-[1-hydroxy-4-(4-hydroxydiphenylmethyl-1-piperidinyl)-butyl]-α,α-dimethylbenzeneacetate, 4-[1-hydroxy-4-(4-hydroxydiphenylmethyl-1-piperidinyl)butyl]-α,α-dimethylbenzeneacetic acid, and 1-[p-(2-hydroxymethyl-2-propyl)phenyl]-4-[4-(α-hydroxy-α-phenylbenzyl)-1-piperidinyl]butanol (hereinafter metabolic derivatives of terfenadine) are effective antihistamines which avoid adverse effects which are associated with the administration of terfenadine, including but not limited to cardiac arrhythmias, sedation, gastrointestinal distress, dry mouth, and constipation or diarrhea. It has also been discovered that these pharmaceutical compositions containing metabolic derivatives of terfenadine are useful in treating allergic disorders and such other conditions as may be related to the composition's activity as an antihistamine, including but not limited to allergic rhinitis, solar urticaria, and symptomatic dermographism, while avoiding the above-described adverse effects associated with the administration of terfenadine. The present invention also includes methods for treating the above-described conditions in a human while avoiding the adverse effects that are associated with terfenadine, by administering the metabolic derivatives to said human.

Furthermore, it has now also been discovered that the metabolic derivatives of terfenadine are useful in treating asthma while avoiding the adverse effects associated with administration of terfenadine. Also, these metabolic derivatives are useful for the treatment of motion sickness and vertigo, while avoiding the adverse effects associated with administration of terfenadine. In addition, the metabolic derivatives of terfenadine are useful in treating such disorders as retinopathy and small vessel disorders associated with diabetes mellitus while avoiding the adverse effects associated with administration of terfenadine.

It has also been discovered that the metabolic derivatives of terfenadine, in combination with non-steroidal anti-inflammatory agents or other non-narcotic analgesics, are useful for the treatment of cough, cold, cold-like and/or flu symptoms and the discomfort, pain, headache, fever, and general malaise associated therewith. The use of pharmaceutical compositions of the invention, containing the metabolic derivatives of terfenadine, and non-narcotic analgesics or non-steroidal anti-inflammatory agents such aspirin, acetaminophen or ibuprofen, may optionally include one or more other active components including a decongestant (such as pseudoephedrine), a cough suppressant/antitussive (such as dextromethorphan) or an expectorant (such as guaifenesin).

DETAILED DESCRIPTION OF THE INVENTION

The present invention encompasses a method of treating a human afflicted by or susceptible to an allergic disorder while avoiding the concomitant liability of adverse effects associated with the administration of terfenadine, which comprises administering to said human afflicted by or susceptible to an allergic disorder an amount of one or more compounds selected from a class of metabolic derivatives of terfenadine, or a pharmaceutically acceptable salt thereof, said amount being sufficient to treat said allergic disorder, but insufficient to cause the adverse effects associated with terfenadine. Suitable metabolic derivatives are compounds selected from the group consisting of methyl 4-[1-hydroxy-4-(4-hydroxydiphenylmethyl-1-piperidinyl)butyl]-α,α-dimethylbenzeneacetate, 4-[1-hydroxy-4-(4-hydroxydiphenylmethyl-1-piperidinyl)butyl]-α,α-dimethylbenzeneacetic acid, 1-[p-(2-hydroxymethyl-2-propyl)phenyl]-4-[4-(α-hydroxy-α-phenylbenzyl)-1-piperidinyl]butanol, and the like.

The present invention also encompasses a composition adapted for the treatment of a human having an allergic disorder which comprises an amount of a metabolic derivative of terfenadine, or a pharmaceutically acceptable salt thereof, said amount being sufficient to alleviate said allergic disorder but insufficient to cause the adverse effects associated with terfenadine.

The present invention further encompasses a method of treating asthma in a human, while avoiding the concomitant liability of adverse effects associated with the administration of terfenadine, which comprises administering to said human afflicted by asthma an amount of a metabolic derivative of terfenadine or a pharmaceutically acceptable salt thereof, said amount being sufficient to alleviate said asthma but insufficient to cause the adverse effects associated with terfenadine. Suitable metabolic derivatives of terfenadine are compounds selected from the group consisting of methyl 4-[1-hydroxy-4-(4-hydroxydiphenylmethyl-1-piperidinyl)-butyl]-α,α-dimethylbenzeneacetate, 4-[1-hydroxy-4-(4-hydroxydiphenylmethyl-1-piperidinyl)butyl]-α,α-dimethylbenzeneacetic acid, 1-[p-(2-hydroxymethyl-2-propyl)phenyl]-4-[4-(α-hydroxy-α-phenylbenzyl)-1-piperidinyl]butanol, the like.

In addition, the present invention encompasses compositions adapted for the treatment of a human having asthma which comprises an amount of a metabolic derivative of terfenadine, or a pharmaceutically acceptable salt thereof, said amount being sufficient to alleviate said asthma but insufficient to cause the adverse effects associated with terfenadine.

A further aspect of the present invention includes a method of treating motion sickness or vertigo in a human, while avoiding the concomitant liability of adverse effects associated with the administration of terfenadine, which comprises administering to said human afflicted by motion sickness or vertigo an amount of a metabolic derivative of terfenadine, or a pharmaceutically acceptable salt thereof, said amount being sufficient to alleviate said motion sickness or vertigo but insufficient to cause the adverse effects associated with terfenadine. Suitable metabolic derivatives of terfenadine are compounds selected from the group consisting of methyl 4-[1-hydroxy-4-(4-hydroxydiphenylmethyl-1-piperidinyl)butyl]-α,α-dimethylbenzeneacetate, 4-[1-hydroxy-4-(4-hydroxydiphenylmethyl-1-piperidinyl)-butyl]-α,α-dimethylbenzeneacetic acid, 1-[p-(2-hydroxymethyl-2-propyl)phenyl]-4-[4-(α-hydroxy-α-phenylbenzyl)-1-piperidinyl]butanol, and the like.

Furthermore, the present invention includes compositions for treating motion sickness or vertigo in a human which comprises an amount of a metabolic derivative of terfenadine, or a pharmaceutically acceptable salt thereof, said amount being sufficient to alleviate said motion sickness or vertigo but insufficient to cause the adverse effects associated with terfenadine.

Also included in the present invention is a method of treating retinopathy or other small vessel diseases associated with diabetes mellitus while avoiding the concomitant liability of adverse effects associated with the administration of terfenadine, which comprises administering to said human an amount of a metabolic derivative of terfenadine, or a pharmaceutically acceptable salt thereof, said amount being sufficient to alleviate said retinopathy or other small vessel diseases associated with diabetes mellitus but insufficient to cause the adverse effects associated with terfenadine. Suitable metabolic derivatives of terfenadine are compounds selected from the group consisting of methyl 4-[1-hydroxy-4-(4-hydroxydiphenylmethyl-1-piperidinyl)-butyl]-α,α-dimethylbenzeneacetate, 4-[1-hydroxy-4-(4-hydroxydiphenylmethyl-1-piperidinyl)butyl]-α,α-dimethylbenzeneacetic acid, 1-[p-(2-hydroxymethyl-2-propyl)phenyl]-4-[4-(α-hydroxy-α-phenylbenzYl)-1-piperidinyl]butanol, and the like.

Additionally, the present invention includes compositions for treating retinopathy or other small vessel diseases associated with diabetes mellitus in a human, comprising an amount of a metabolic derivative of terfenadine, or a pharmaceutically acceptable salt thereof, said amount being sufficient to alleviate said retinopathy or other small vessel diseases associated with diabetes mellitus but insufficient to cause the adverse effects associated with terfenadine.

Furthermore, the present invention includes a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of terfenadine, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Additionally, the present invention includes a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of terfenadine, with (ii) a therapeutically effective amount of a decongestant such as pseudoephedrine, or pharmaceutically acceptable salts thereof.

The present invention further encompasses a method for the treatment of cough, cold, cold-like, and/or flu symptoms and the discomfort, pain, fever, and general malaise associated therewith, in a human in need of such treatment, by administering to said human a composition comprising (i) a therapeutically effective amount of at least one metabolic derivative of terfenadine, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Additionally, the present invention encompasses a method for the treatment of cough, cold, cold-like, and/or flu symptoms and the discomfort, pain, fever, and general malaise associated therewith, in a human in need of such treatment comprising administering to said human a composition comprising (i) a therapeutically effective amount of at least one metabolic derivative of terfenadine with (ii) a therapeutically effective amount of a decongestant such as pseudoephedrine, or pharmaceutically acceptable salts thereof.

A further aspect of this invention includes a method of treating an allergic reaction in a human with a composition comprising (i) a therapeutically effective amount of at least one metabolic derivative of terfenadine, with (ii) a therapeutically effective amount of at least one non-steroidal anti-inflammatory agent or non-narcotic analgesic such as acetylsalicylic acid, acetaminophen, ibuprofen, ketoprofen, and naproxen, or pharmaceutically acceptable salts thereof.

Furthermore, the present invention includes a method of treating an allergic reaction in a human with a composition comprising (i) a therapeutically effective amount of at least one metabolic derivative of terfenadine, with (ii) a therapeutically effective amount of a decongestant such as pseudoephedrine, or pharmaceutically acceptable salts thereof.

Terfenadine has antihistaminic activity and provides therapy and a reduction of symptoms for a variety of conditions and disorders related to allergic disorders, diabetes mellitus and other conditions; however, this drug, while offering the expectation of efficacy, causes adverse effects. Utilizing the metabolic derivatives of terfenadine results in clearer dose-related definitions of efficacy, diminished adverse effects, and accordingly, an improved therapeutic index. It is, therefore, more desirable to use metabolic derivatives of terfenadine than to use terfenadine itself.

The term "adverse effects" includes, but is not limited to cardiac arrhythmias, sedation, gastrointestinal distress, dry mouth, constipation, and diarrhea. The term "cardiac arrhythmias" includes, but is not limited to ventricular tachyarrhythmias, torsades de pointes, and ventricular fibrillation.

The phrase "therapeutically effective amount" means that amount of one or more of the metabolic derivatives of terfenadine which provides a therapeutic benefit in the treatment or management of allergic disorders, asthma, retinopathy or other small vessel disorders associated with diabetes mellitus, motion sickness, vertigo, or cough, cold, cold-like, and/or flu symptoms and the discomfort, pain, fever, and general malaise associated therewith. Examples of allergic disorders include, but are not limited to, allergic rhinitis, solar urticaria, and symptomatic dermographism. The symptoms associated with these allergic disorders and the cough, cold, cold-like, and/or flu symptoms include, but are not limited to, sneezing, rhinorrhea, lacrimation, and dermal irritation. The term "asthma" is defined as a disorder characterized by increased responsiveness of the trachea and bronchi to various stimuli which results in symptoms which include wheezing, cough, and dyspnea. The term "vertigo" as used herein means dizziness associated with, but not limited to motion, height, and changes in body position. The term "diabetic retinopathy" or "retinopathy associated with diabetes mellitus" is that disorder caused by increased permeability of the capillaries in the eye which leads to hemorrhages and edema in the eye and can lead to blindness. The term "small vessel disorders associated with diabetes mellitus" includes, but is not limited to diabetic retinopathy and peripheral vascular disease.

The magnitude of a prophylactic or therapeutic dose of the metabolic derivatives of terfenadine in the acute or chronic management of disease will vary with the severity of the condition to be treated and the route of administration. The dose, and perhaps the dose frequency, will also vary according to the age, body weight, and response of the individual patient. In general, the total daily dose range, for the conditions described herein, is from about 0.01 mg to about 500 mg administered in single or divided doses orally, topically, transdermally, or locally by aerosol. For example, a preferred oral daily dose range should be from about 1 mg to about 500 mg, while most preferably an oral daily dose range should be between about 20 mg and about 200 mg. It is further recommended that children, patients aged over 65 years, and those with impaired renal or hepatic function initially receive low doses, and that they then be titrated based on individual response(s) or blood level(s). It may be necessary to use dosages outside these ranges in some cases as will be apparent to those skilled in the art. Further, it is noted that the clinician or treating physician will know how and when to interrupt, adjust, or terminate therapy in conjunction with individual patient response.

The various terms "an amount sufficient to alleviate said allergic disorder but insufficient to cause said adverse effects," "an amount sufficient to alleviate said asthma but insufficient to cause said adverse effects," "an amount sufficient to alleviate said motion sickness but insufficient to cause said adverse effects," and "an amount sufficient to alleviate said retinopathy or other small vessel diseases associated with diabetes mellitus but insufficient to cause said adverse effects" are encompassed by the above-described dosage amounts and dose frequency schedule. In addition, the terms "a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of terfenadine, with (ii) a therapeutically effective amount of at least one non-steroidal anti-inflammatory agent or non-narcotic analgesic" and "a pharmaceutical composition for use in the treatment of cough, cold, cold-like and/or flu symptoms and the discomfort, pain, fever and general malaise associated therewith, in a human, said composition comprising (i) a therapeutically effective amount of at least one metabolic derivative of terfenadine, with (ii) a therapeutically effective amount of a decongestant," as well as the term "therapeutically effective amount of at least one of the $\alpha$-aryl-4-substituted piperidinoalkanol derivatives" are also encompassed by the above-described dosage amounts and dose frequency schedule.

Any suitable route of administration may be employed for providing the patient with an effective dosage of the metabolic derivatives of terfenadine. For example, oral, rectal, parenteral, transdermal, subcutaneous, intramuscular, and like forms of administration may be employed. Dosage forms include tablets, troches, dispersions, suspensions, solutions, capsules, patches, and the like.

The pharmaceutical compositions of the present invention comprise the metabolic derivatives of terfenadine as active ingredient, or a pharmaceutically acceptable salt thereof, and may also contain a pharmaceutically acceptable carrier, and optionally, other therapeutic ingredients.

The term "pharmaceutically acceptable salts" refers to salts prepared from pharmaceutically acceptable non-toxic acids or bases including inorganic acids or bases or organic acids or bases. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucoronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases include metallic salts made from aluminum, calcium, lithium, magnesium, potassium, sodium, and zinc. Appropriate organic bases may be selected, for example, from N,N'-dibenzylethylenediamine, chloroprocaine, choline, diethanolamine, ethylenediamine, meglumaine (N-methylglucamine), lysine and procaine.

The compositions of the present invention include compositions such as suspensions, solutions and elixirs; aerosols; or carriers such as starches, sugars, microcrystalline cellulose, diluents, granulating agents, lubricants, binders, disintegrating agents, and the like, in the case of oral solid preparations (such as powders, capsules, and tablets), with the oral solid preparations being preferred over the oral liquid preparations. The most preferred oral solid preparations are tablets.

Because of their ease of administration, tablets and capsules represent the most advantageous oral dosage unit form, in which case solid pharmaceutical carriers are employed. If desired, tablets may be coated by standard aqueous or nonaqueous techniques.

In addition to the common dosage forms set out above, the compounds of the present invention may also be administered by controlled release means and/or delivery devices such as those described in U.S. Pat. Nos. 3,845,770; 3,916,899; 3,536,809; 3,598,123; and 4,008,719, the disclosures of which are hereby incorporated by reference.

Pharmaceutical compositions of the present invention suitable for oral administration may be presented as discrete units such as capsules, cachets, or tablets, or aerosol sprays, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent. Desirably, each tablet contains from about 10 mg to about 150 mg of the active ingredient, and each cachet or capsule contains from about 10 mg to about 150 mg of the active ingredient, i.e., a metabolic derivative of terfenadine. Most preferably, the tablet, cachet or capsule contains either one of three dosages, 30 mg, 60 mg or 90 mg of the active ingredient.

The invention is further defined by reference to the following examples describing in detail the preparation of the compound and the compositions of the present invention, as well as their utility. It will be apparent to those skilled in the art that many modifications, both to materials and methods, may be practiced which are within the scope of this invention.

EXAMPLES

Example 1

A. Preparation of methyl 4-[1-hydroxy-4-(4-hydroxydiphenylmethyl-1-piperidinyl)butyl]-α,α-dimethylbenzeneacetate.

4-(α-Hydroxy-α-phenylbenzyl)piperidine (4.3 gm) was combined with methyl p-(4-chloro-1-oxobutyl)-α,α-dimethylbenzeneacetate (4.5 gm), potassium bicarbonate (2.9 gm), potassium iodide (ca. 50 mg), and methyl isobutyl ketone (50 ml) and heated to reflux for 48 hours. Additional 4-(α-hydroxy-α-phenylbenzyl)-piperidine (1.1 gm) was added, and heating was continued for an additional 48 hours. Upon cooling the mixture to room temperature, water was added and the pH of the solution was adjusted to ca. 12 by addition of aqueous sodium hydroxide. The mixture was extracted with ethyl acetate. The ethyl acetate solution was washed with saturated aqueous sodium bicarbonate and brine and dried over sodium sulfate. The ethyl acetate was removed on a rotary evaporator and the residue was treated with 25% ethyl acetate in hexane. The resulting precipitate was filtered and air dried to give methyl 4-[1-oxo-4-(4-hydroxydiphenylmethyl-1-piperidinyl)butyl]-α,α-dimethylbenzeneacetate. This intermediate precipitate (2.4 gm) was combined with tetrahydrofuran (10 ml) and borane in tetrahydrofuran (5 ml) and stirred for 48 hours. Methanol (10 ml) and sodium bicarbonate (1.5 gm) were added to the reaction solution, and the mixture was stirred for 12 hours. The mixture was diluted with ethyl acetate (200 ml) and washed with saturated aqueous sodium bicarbonate to give methyl R-4-[1-hydroxy-4-(4-hydroxydiphenylmethyl-1-piperidinyl)butyl]-α,α-dimethylbenzeneacetate.

B. 4-[1-hydroxy-4-(4-hydroxydiphenylmethyl-1-piperidinyl)butyl]-α,α-dimethylbenzeneacetic acid [terfenadine carboxylate].

Methyl 4-[1-hydroxy-4-(4-hydroxydiphenylmethyl-1-piperidinyl)butyl]-α,α-dimethylbenzeneacetate (1.2 gm) was combined with potassium hydroxide (0.4 gm) and ethanol (5 ml), and the mixture was heated to reflux for 7 hours. The ethanol was removed on a rotary evaporator and the residue was dissolved in water (2 ml). The aqueous solution was acidifed with glacial acetic acid to provide a solid which was recrystallized from 1:1 methanol/ethyl acetate to give 4-[1-hydroxy-4-(4-hydroxydiphenylmethyl-1-piperidinyl)butyl]-α,α-dimethylbenzeneacetic acid (terfenadine carboxylate).

Example 2

Activities of various species of terfenadine and its metabolites at the histamine $H_1$-receptor were assessed using the [$^3$H]pyrilamine binding assay as described in Chang et al., J. Neurochem. 32:1653–1663 (1979). Briefly, membranes from bovine cerebellum were incubated with [$^3$H]pyrilamine and varying concentrations of test compound. The reactions were carried out in 50 mM sodium phosphate buffer (pH 7.5) at 25° C. for 30 minutes. The reaction was terminated by rapid vacuum filtration onto glass fiber filters. Radioactivity trapped on the filters was determined and compared to control values to acertain the interaction of the test compound with the $H_1$-receptor. Results were as follows:

| Compound | Percent Inhibition (at various concentrations) | | |
|---|---|---|---|
| | $10^{-9}$M | $10^{-7}$M | $10^{-5}$M |
| R,S-terfenadine | 11.0 | 28.7 | 86.9 |
| R-(+)-terfenadine | 11.4 | 19.4 | 90.3 |
| R-(+)-terfenadine carboxylate | 12.4 | 45.2 | 87.3 |
| S-(−)-terfenadine | 3.2 | 24.4 | 92.8 |
| S-(−)-terfenadine carboxylate | 8.1 | 54.1 | 88.7 |

Example 3

Single ventricular myocytes were obtained from isolated cat hearts by conventional techniques. The rod-shaped single cells were maintained in a HEPES buffer and they were "patch clamped" using suction pipettes. A Patch-Clamp L/M-PEC 7 amplifier was used to record current tracings and the recording electrodes were filled with a solution of potassium aspartate. Voltage clamp pulses and data acquisition were controlled by a Sperry PC/IT Computer running P Clamp software. A minimum of 4 cells were studied at each test concentration of the following drugs: racemic terfenadine, racemic terfenadine carboxylate, and quinidine (as a reference compound). Results were as follows:

| | Conc (uM) | Block of the delayed rectifier potassium current (%) |
|---|---|---|
| Terfenadine | 0.01 | 12 ± 9.3 |
| | 0.10 | 39.5 ± 9.8 |
| | 1.00 | 92.6 (92.5; 92.8) |
| Terfenadine carboxylate | 0.01 | 0 ± 0 |
| | 0.10 | 0 ± 0 |
| | 1.00 | 0 ± 0 |

Example 4

Oral Formulation - Capsules:

| Formula | Quantity per capsule in mg. | | |
|---|---|---|---|
| | A | B | C |
| Active ingredient Terfenadine carboxylate | 30.0 | 60.0 | 90.0 |
| Starch 1500 | 69.0 | 39.0 | 9.0 |
| Magnesium Stearate BP | 1.0 | 1.0 | 1.0 |
| Compression Weight | 100.0 | 100.0 | 100.0 |

The active ingredient is sieved and blended with the excipients. The mixture is filled into suitably sized two-piece hard gelatin capsules using suitable machinery. Other doses may be prepared by altering the fill weight and if necessary, changing the capsule size to suit.

Example 5

Oral Formulation - Tablets:

| Formula | Quantity per Tablet in mg. | | |
|---|---|---|---|
| | A | B | C |
| Active ingredient, Terfenadine Carboxylate | 30.0 | 60.0 | 90.0 |
| Lactose BP | 123.5 | 93.5 | 63.5 |
| Starch BP | 30.0 | 30.0 | 30.0 |
| Pregelatinized Maize Starch BP | 15.0 | 15.0 | 15.0 |
| Magnesium stearate | 1.5 | 1.5 | 1.5 |
| Compression Weight | 200.0 | 200.0 | 200.0 |

The active ingredient, is sieved through a suitable sieve and blended with the lactose until a uniform blend is formed. Suitable volumes of water are added and the powders are granulated. After drying, the granules are then screened and blended with the magnesium stearate. The resulting granules are then compressed into tablets of desired shape. Tablets of other strengths may be prepared by altering the ratio of active ingredient to the excipient(s) or the compression weight.

What is claimed is:

1. A method of treating allergic rhinitis in a human while avoiding the concomitant liability of cardiac arrhythmias associated with the administration of terfenadine, comprising administering to said human a therapeutically effective amount of racemic terfenadine carboxylate or a pharmaceutically acceptable salt thereof.

2. The method of claim 1 wherein the amount of racemic terfenadine carboxylate administered is from about 1 mg to about 500 mg per day.

3. The method of claim 2 wherein the amount of racemic terfenadine carboxylate administered is from about 20 mg to about 200 mg per day.

4. The method of claim 1 wherein the amount of said racemic terfenadine carboxylate pharmaceutically acceptable salt thereof is administered together with a pharmaceutically acceptable carrier.

5. A method of treating allergic rhinitis in a human while avoiding the concomitant liability of cardiac arrhythmias associated with the administration of terfenadine, comprising administering to said human a composition comprising (i) a therapeutically effective amount of racemic terfenadine carboxylate or a pharmaceutically acceptable salt thereof, and (ii) a therapeutically effective amount of a nonsteroidal anti-inflammatory agent or non-narcotic analgesic.

6. A method of treating allergic rhinitis in a human while avoiding the concomitant liability of cardiac arrhythmias associated with the administration of terfenadine, comprising administering to said human a composition comprising (i) a therapeutically effective amount of racemic terfenadine carboxylate or a pharmaceutically acceptable salt thereof, and (ii) a therapeutically effective amount of a decongestant.

* * * * *

Adverse Decisions In Interference

Patent No. 5,375,693, Raymond L. Woosley, James W. Young, Yiwang Chen, METHOD AND COMPOSITIONS FOR TREATING ALLERGIC DISORDERS AND OTHER DISORDERS METABOLIC DERIVATIVES OF TERFENADINE, Interference No. 103,875, final judgment adverse to the patentees rendered November 2, 1999, as to claims 1-6.

*(Official Gazette May 2, 2000)*